United States Patent
Wawro et al.

[11] Patent Number: 5,838,424
[45] Date of Patent: Nov. 17, 1998

[54] VIEW PORT FOR EYE TEST APPARATUS

[75] Inventors: Marcia J. Wawro, Auburn; William R. Witkowski, Marcellus, both of N.Y.

[73] Assignee: Welch Allyn, Inc., Skaneateles Falls, N.Y.

[21] Appl. No.: 806,913

[22] Filed: Feb. 26, 1997

[51] Int. Cl.$^6$ .................................................. A61B 3/00
[52] U.S. Cl. ........................................ 351/245; 351/200
[58] Field of Search .................................... 351/245, 200, 351/246, 205, 206, 208, 222, 224, 226

[56] References Cited

U.S. PATENT DOCUMENTS

5,459,536  10/1995  Shalon et al. .......................... 351/226

Primary Examiner—Hung X. Dang
Attorney, Agent, or Firm—Wall Marjama Bilinski & Burr

[57] ABSTRACT

In an eye test apparatus of the type having a single examination area, an improved view port is disclosed having a view port casing and a mounting apparatus arranged so that the view port casing is movable between a first and second active positions. In a first active position, the casing receives a patient's forehead so that a patient's right eye is aligned with a examination area, and a second active position wherein a casing receives a patient's forehead so that a patient's left eye is aligned with the examination area. The casing is specially configured to occlude ambient light and to accommodate a patient wearing eyeglasses. The eye test apparatus may further have a position sensor system for sending the present position of the casing. In one embodiment of the invention, a control unit is provided which is responsive to the position sensor system so that administration of a test to a patient is permitted only if the casing is in an active position, and may further be made responsive to the sensor system so that data captured during the test by the control unit is automatically categorized according to which eye is currently being tested.

43 Claims, 7 Drawing Sheets

VIEW PORT FOR EYE TEST APPARATUS

BACKGROUND OF THE INVENTION

1. Field of the Invention

The invention relates generally to eye test apparatuses and in particular to an improved view port for an eye test apparatus.

2. Background of the Prior Art

There are two major types of eye test apparatuses. In a first, passive type of an eye test apparatus (such as a visual field tester or a visual acuity tester), an image is presented to a patient, and the patient is requested to identify features of the image. In a second, active type of eye test apparatus (e.g. a fundus camera or an autorefractor) features of a patient's eye are imaged or characterized by an imaging device such as a camera, or an other device detecting eye characteristics. Because many types of eye testing applications do not require the testing of both eyes at once, it is common in many eye test apparatuses to provide a single examination system. The examination system of an eye test apparatus of the first type may comprises an optical system and a display device, while the examination system of an eye test apparatus of the second type may comprise an imaging device, such as a CCD imager, and an associated optical system. In either type of eye test apparatus, the examination system includes an exposed, examination area portion, which is aligned to the patient's eye during testing.

In use of eye test apparatuses having a single examination area, a patient's right eye must first be aligned with the examination area for testing of the right eye, and then the patient's left eye is aligned with the examination area for testing of the left eye. It is common in use of these apparatuses to block the eye not being tested with a patch or other blocking device.

A first major problem observed with existing single examination area eye test apparatuses involves the aligning of the eyes with the examination area. Alignment devices of the prior art have been noted to be difficult and time consuming and to operate, and further, fail to position a head in the correct position in many cases.

Another problem with existing eye test apparatuses is that they fail to provide adequate occlusion of images other than the image (which may be simply the camera lens and light source in the case of an active type test apparatus) emanating from the test apparatus. Test results can be erroneous if an eye being tested by a patient is exposed to a light source other than the test apparatus light source. It is common in the prior art to institute cumbersome test procedures (such as darkening an entire examination room and/or patching the eye not being tested during testing) in order to ensure adequate occlusion.

Still another problem with many prior art eye test apparatuses is that they require the positioning of an eye proximate an examination area such that it is difficult or impossible for a patient to wear eye glasses during testings. This, of course, prevents the testing of the impact that a corrective eye glass lens has on a patient's vision or eye characteristics or requires separate correction means.

There are further limitations in prior art eye test apparatuses involving apparatus control. For example, in the prior art, it is necessary for an operator to manually activate control inputs to begin a testing cycle, to end a testing cycle, and to correlate data that is collected with the eye being tested. In controlling existing test apparatuses, the operator must repeatedly monitor the alignment of a patients eye, and observe, which eye is being tested, before imparting control to begin, end, or correlate collected data. The intensity of the manual control required for operating prior art apparatuses, makes such devices susceptible to operational error.

There exists a need for an easy-to-operate eye test apparatus having a single examination system, which provides improved alignment, stability, and image occlusion over prior art apparatuses, which accommodates a patient wearing eyeglasses, and which is of a simple, low cost design.

SUMMARY OF THE INVENTION

According to its major aspects and broadly stated, the present invention relates, in one aspect, to a view port for an eye testing apparatus having a single examination area. In another aspect, the invention relates to an eye test apparatus having a main control unit for controlling the administration of a test to a user, which is responsive to a sensor system for sensing the present position of a view port casing of the eye test unit.

In the present invention a view port including a casing having a formation for receiving a patient's forehead is disposed forward of an eye testing apparatus's examination area. The view port includes a mounting apparatus and casing arranged so that the casing is slidable between a first active position wherein the view port casing receives a patient's head so that a patient's right eye is aligned correctly forward of the examination area, and a second active position wherein the view port casing receives a patient's forehead so that a patient's left eye is aligned correctly forward of the examination area. Positioning between the first and second active positions are considered intermediate, or inactive positions.

A view port casing designed according to the invention should occlude patient's vision of images or light rays other than images and light emanating from the apparatus, and also is preferably configured to accommodate a patient wearing eye glasses.

Sophisticated eye test apparatuses have a main control unit, typically comprising a program controlled microcomputer, for controlling the administration of a test to a user. In a visual field test apparatus, for example, a microcomputer controls the driving of a series of images on a cathode ray tube, which a user is requested to identify. Sophisticated eye test units typically also have data output and/or storage components for outputting and/or recording data captured during administration of a test.

In one embodiment of the present invention, a control unit of an eye test unit is made responsive to signals generated by a position sensor system having one or more position sensors which sense the position of a view port casing in relation to a examination area. Specifically, in one embodiment, a pair of position sensors are arranged on the view port for determining whether the view port is in a first position, a second position, or in an intermediate position.

The signals from these sensors are, in turn, input into the eye test apparatus control unit. The control unit can be made responsive to the position sensor system in a variety of useful ways. For example, the control unit can be made responsive to a position sensor system so that commencing of an eye test is permitted only if the viewing port is in one of either a first or second position. The control unit can also be made responsive to the position sensing system so that data is automatically categorized as either left eye or right eye data without requiring that manual control be input by a human test administrator. The control unit can also be made responsive to a sensor system so that test administration is abandoned or paused if the casing becomes misaligned during test administration.

These and other features and advantages of the invention will become clear to the skilled artisan from a reading of Detailed Description of the Preferred Embodiments in connection with the referenced drawings.

DETAILED DESCRIPTION OF THE PREFERRED EMBODIMENTS

Figure 1A:
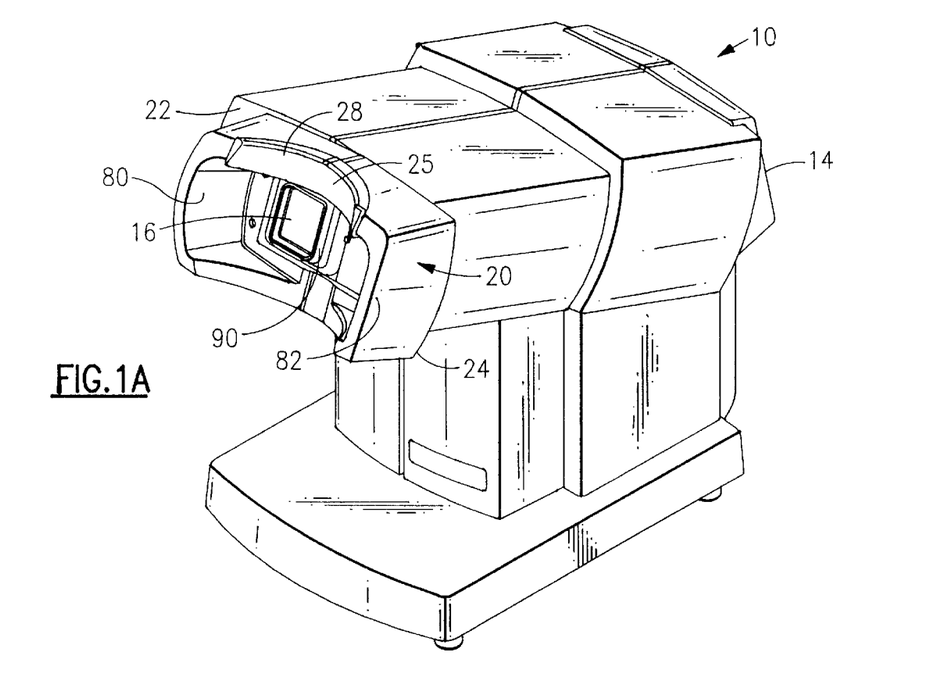
FIG. 1A is a perspective view of a visual field test apparatus in which the present invention may be incorporated.
Figure 1B:
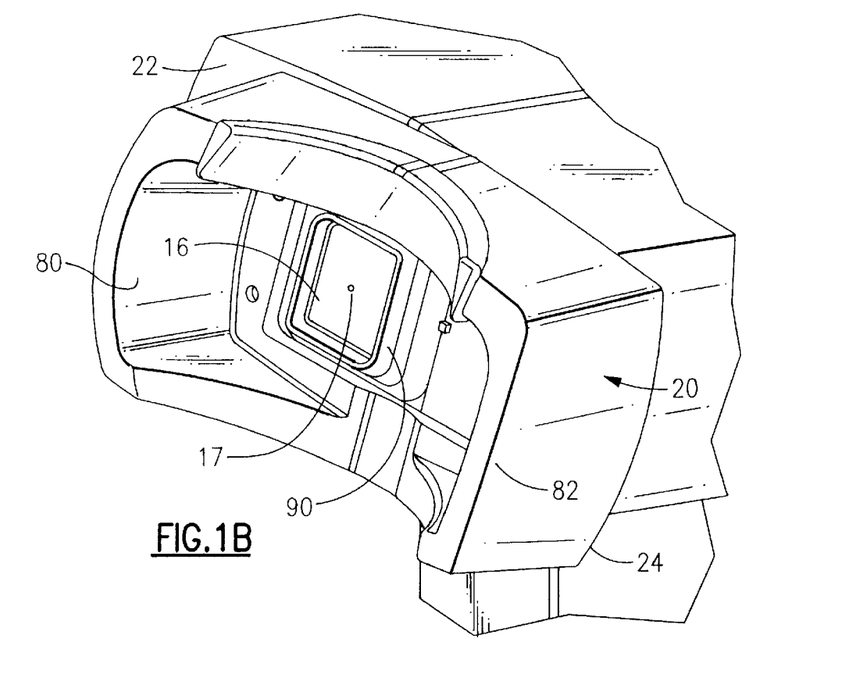
FIG. 1B is an exploded view of a view port according to the invention incorporated in an eye test apparatus.
Figure 2:
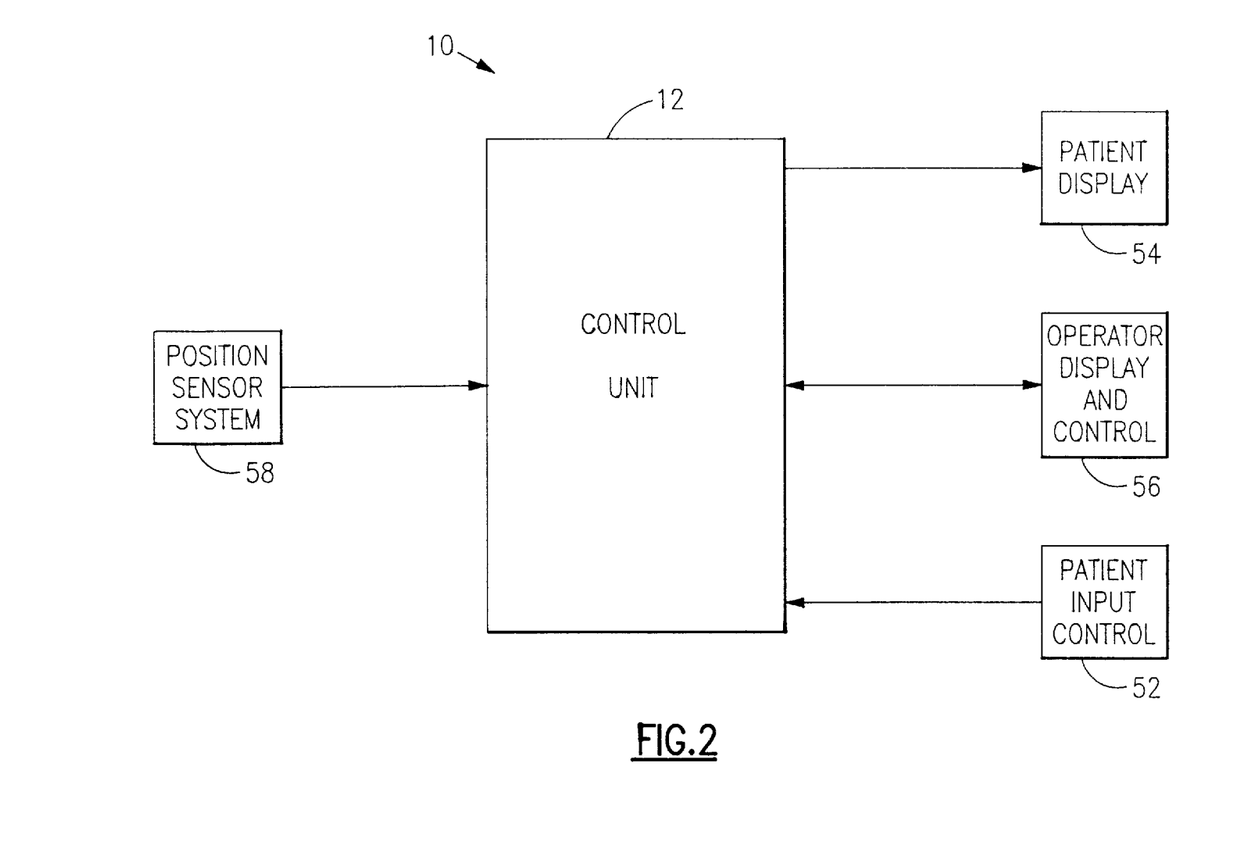
FIG. 2 is a block diagram illustrating electrical connections of a control system controlling an eye test apparatus.

An eye test apparatus of the type in which the present invention may be incorporated is shown in FIGS. 1 and 2. Perspective drawing FIG. 1 and block diagram FIG. 2 illustrate a visual field tester 10 having an examination system (partially shown) and control unit 12 for controlling operation of the apparatus. The examination system includes a cathode ray tube (CRT) located inside housing 14, or other type of display terminal, and a optical system for focusing images from the CRT onto a patient's eye. The outer surface or edge of the lens system defines a examination area 16. During testing of an eye, a patient's eye is positioned forward of the examination area.

As is the case with many types of eye test apparatuses, visual field eye test apparatus 10 includes a single examination system. While features of the invention are especially well suited for use in a visual field test apparatus, persons skilled in the art will recognize that at least some features of the invention can be incorporated into other types of eye test units including, for example, visual field eye test apparatuses and visual acuity eye test apparatuses. The present invention can also be incorporated into active type eye test apparatuses such as a fundus camera and autorefractor eye test apparatuses.

Referring now to specific aspects of the present invention, the present invention includes a component for aiding in the alignment of a patient's eyes during eye testing in an eye test apparatus having a single viewing system. Namely, as seen in FIGS. 3 through 6, the present invention includes an improved view port 20 for stabilizing and aligning of a patient's head in an eye testing apparatus having a single examination area, and for occluding a patient's vision from interfering light and images.

View port 20 is mounted on face 22 of housing 14 forward of an examination area, and includes a mounting apparatus 24 and a casing 26. Formed on view port casing 26 is a top formation 28 typically of a curved shape, for receiving a patient's forehead. Formation 28 is preferably formed with an appropriate curvature in accordance with the natural curvature of a human forehead so that when a patient's forehead is received therein, the center of a patient's forehead is guided generally toward the center point 25 of formation 28. While the casing shown in FIGS. 3–6 includes a top formation for receiving and contacting a patient's forehead, casing 26 may also be formed to receive another point of a patient's head and still provide stabilization and alignment of a head.

Referring to further aspects of a preferred casing design it is seen that casing 26 may include peripheral walls 80, 82 top wall 84 and bottom wall 86. For occlusion of outside light and images from a patient's vision, the edges of peripheral walls 80 and 82 top and bottom wall 84 and 86 should extend outwardly at least to a point so that when a patient's head is received in the casing the edges of the walls are approximately in a plane with the outer surface of a patient's eyes. Bottom wall 86 includes a bottom formation 88 configured to accommodate a patient's nose during testing. For further improving the occlusion of stray light rays from a patient's vision, the entire interior surface of casing 26, and of the portion of housing face 22 exposed to the casing interior should be light absorbing color such as black. Designed as described, casing 26 sufficiently prevents intrusion of ambient light into casing 26 so as to make it unnecessary to apply a patch or blocking device to an untested eye during administration of a test. Light from apparatus 10 can be occluded from the vision of an untested eye by providing a shield 90 about the perimeter of examination area 16, preferably of a frustroconical or frustropyramidal configuration as shown.

In order to comfortably accommodate a head of a patient wearing eyeglasses, the depth, width, and height of view port casing 26 should be dimensioned so that substantially no portion of casing 26 contacts an eyeglass frame when a patient's forehead is received in top formation 28. To accommodate a patient wearing small commercially available eye glass frames, casing should be dimensioned to a width of at least about 6.9 inches, a height (from top to bottom) of about 3.2 inches, and depth (as measured from the shallowest point 25 of top formation to casing base 29) of about 1.7 inches if the examination area does not include a shield 90 disposed thereabout. The depth dimension requirement depends on the depth of light shield 90 disposed about examination area 16, if one is present. If the examination area has a shield 90 disposed thereabout, casing 26 should be sized so that the distance from the plane defined by shallowest point 25 to the top shield 90 is no less than about 0.5 inches for the view port to accommodate patient's wearing small sized commercially available eyeglasses. While casing 26 is shown as having a generally rectangular configuration, casing may have another configuration. For example, casing 26 can be substantially oval shaped.

View port casing 26 is moveable between various positions. In one embodiment, view port casing 26 is slidable between a first active position wherein the view port casing receives a patient's forehead so that a patient's right eye is positioned forward of the examination area, and a second active position wherein the view port casing receives a patient's forehead so that a patient's left eye is positioned forward of the examination area. Positions between the first and second active positions are considered intermediate, or inactive positions.

In the embodiment shown in detail in FIGS. 3 through 6, view port casing 26 is slidably mounted on housing 14. View port casing 26 could also be made adjustably mounted to various positions on face 22 by a mounting mechanism that does not provide for sliding between view port casing 26 and housing 14. For example, casing 26 could be adjustably mounted to face 22 with use of, a peg and hole system, hooks, a motorized or unmotorized worm gear, microloop-and-hook (VELCRO) type fasteners, a camming or linkage mechanism, or any other known mechanism for providing movement (either remove and reattach type movement, or movement not requiring detachment) between two bodies.

Specific attributes of a possible sliding type mounting apparatus are described with reference to FIGS. 3 through 6. Mounting apparatus 24 includes base frame 30 and chassis 32 on which view port casing 26 is securely mounted. For allowing sliding between chassis 32 and base frame 30, bar 34 which is rigidly attached to chassis 32, is engaged by holder mounts 36 extending forwardly from base frame 30. Each holder mount 36 may have a bearing 38, such as a nylon bearing, installed therein for encouraging the smooth gliding of bar 34 through holes of the holder mount 36. For mounting of view port 20 on housing 14 base frame 30 may be rigidly attached to an appropriate mounting member on housing face 22.

As best seen in top view (FIG. 5 and 6) bar 34 may have a pair of detents 42, 44 formed therein for receiving a spring loaded pin 46, which is tensioned between base frame 30 and bar 34 so that pin "clicks in" to one or the other detents to secure chassis 32 in either a first of second active position. While varying degrees of error are allowable depending on the type of eye test apparatuses in which the invention is incorporated, the distance from center 25 of formation 28 to the axis 17 of examination area when the casing is in an active position on face 22 is selected according to anthropological data and should be approximately equivalent to one-half the average distance between a pair of pupils of a human.

As illustrated in FIG. 2, many types of sophisticated eye test apparatuses have a control unit, typically comprising a program controlled microcomputer including at least a program memory device, for controlling the administration of a test to a user. With reference to simplified visual field test apparatus block diagram of FIG. 2, control unit 12 may have input thereto various control buttons 56 controlled by an operator, and may be adapted to control the driving of images on a patient display device 54 and on an operator display device. In a visual field type eye test apparatus, control unit 12 is programmed or otherwise controlled to drive a series of images on a patient display device 54 (inside of housing), which a user is requested to identify, and the results of the test are determined by the patient's ability to identify the various images.

In prior art eye test apparatuses of the general type described, an operator must input control instructions via a control unit 56 in order to configure control unit 12 to categorize patient-input data into the appropriate category according to which eye is currently being tested.

As an improvement to the prior art method, the present invention includes a position sensor system 58 for sensing the current position of view port casing 26. Control unit 12, in one embodiment of the invention is configured to be responsive to the position sensor system 58 so that patient-input data is automatically correlated in accordance with the eye currently being tested. In the present invention, data (such as patient-input response data) that is collected during administration of an eye test may be automatically categorized as left eye or right eye by application of well known computer program methods based on the current status of the output of position sensor system 58. Automatically correlating captured data with the output of position sensor system provides many possible advantages. For example, captured data that is displayed or caused to be printed by apparatus 10 can automatically be properly labeled as left eye or right eye data without requiring that any manually input labeling instructions be input by an operator.

Figure 7:
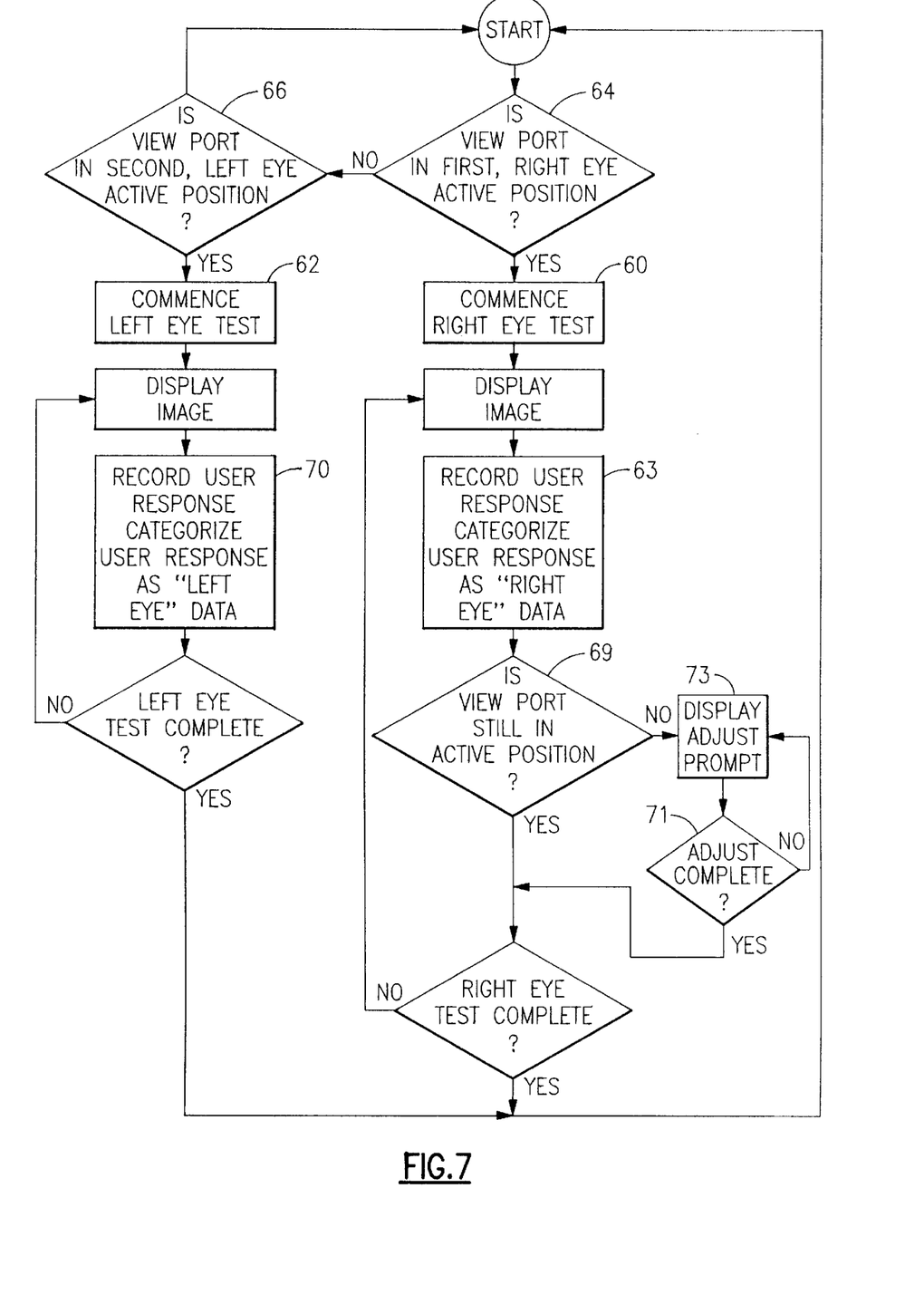
FIG. 7 is a flow diagram illustrating a possible computer program control method for controlling an eye test apparatus according to the invention.

The flow diagram of FIG. 7 illustrates a possible method for controlling an eye test apparatus according to signals generated by a sensor system 58 sensing the position of view port casing 26. It is seen that the control unit will not commence a right eye test at step 60, or a left eye test at step 62 until control unit 12 determines, based on the output of the sensor system, at step 64 or 66 that an active position has been achieved. Once either a right eye test or a left eye test has been commenced, it is seen from step 68 or step 70 that data collected during the test will be properly categorized according which eye is currently being tested.

It is seen further from steps 61 and 63 that when an eye test has been commenced in a visual field type eye test apparatus, or another type of test apparatus, that a series of images may be presented to a patient, which a patient is requested to identify or otherwise respond to. In the present invention, control unit 12 can be made responsive to sensor system 58 so that right-eye specific or left-eye specific visual test pattern or image is presented to a patient depending on the present output state of sensor system 58. The right-eye or left-eye specific test pattern can be selected based on preexisting data pertaining to the patient, or on anthropological data.

According to another aspect of the invention, control unit 12 can be made responsive to the output of position sensor system 58 so that administration of a test to a patient is paused or abandoned in the case where the output of the sensor system indicates that casing 26 is no longer in an active position. Referring to the flow diagram of FIG. 7, control unit 12 at step 69 determines, on a periodic basis during test administration by polling sensor system 58 whether view port casing 26 is still in an active position. If the view port is no longer in an active position, a user may be prompted to correct the position of the casing at steps 71 and 73. The polling method described with reference to FIG. 7 may be replaced with an interrupt type control method, wherein a change in the sensor system output generates an interrupt signal to cause branching of program control. Position verification step 69 shown as being executed during testing of a right eye can be executed during testing of a left eye. While FIG. 7 shows a flow diagram for a visual field tester, it will be recognized that the type of instructions in a program for controlling apparatus 10 will vary depending on the type of apparatus. For example, for incorporation of the invention into an active type eye test apparatus such as a fundus camera, eye image sensor image data may be correlated with the eye being tested at steps 68, 70, and not patient response data as shown.

Figure 3:
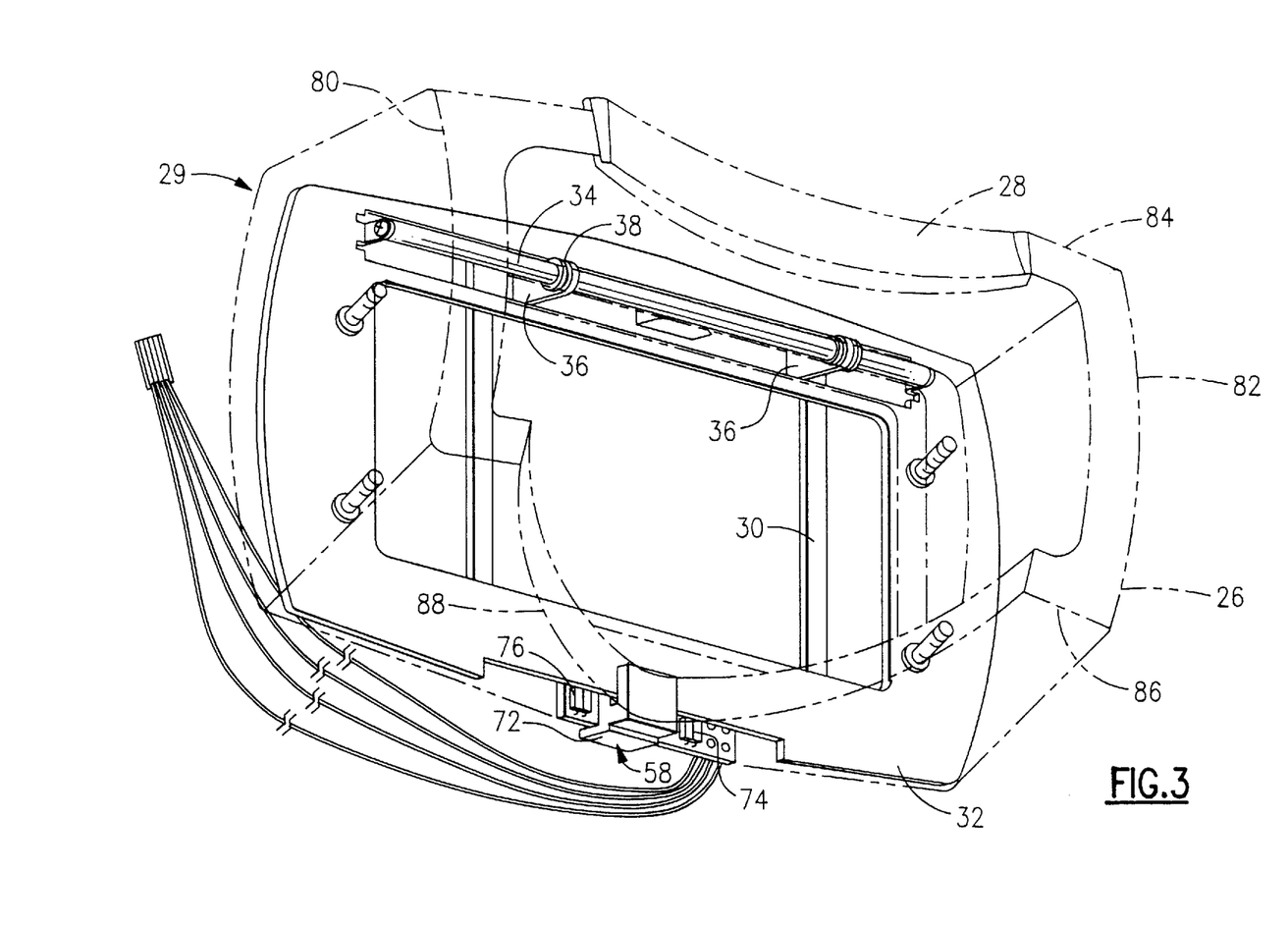
FIG. 3 is a front perspective view of a view port according to the invention.
Figure 4:
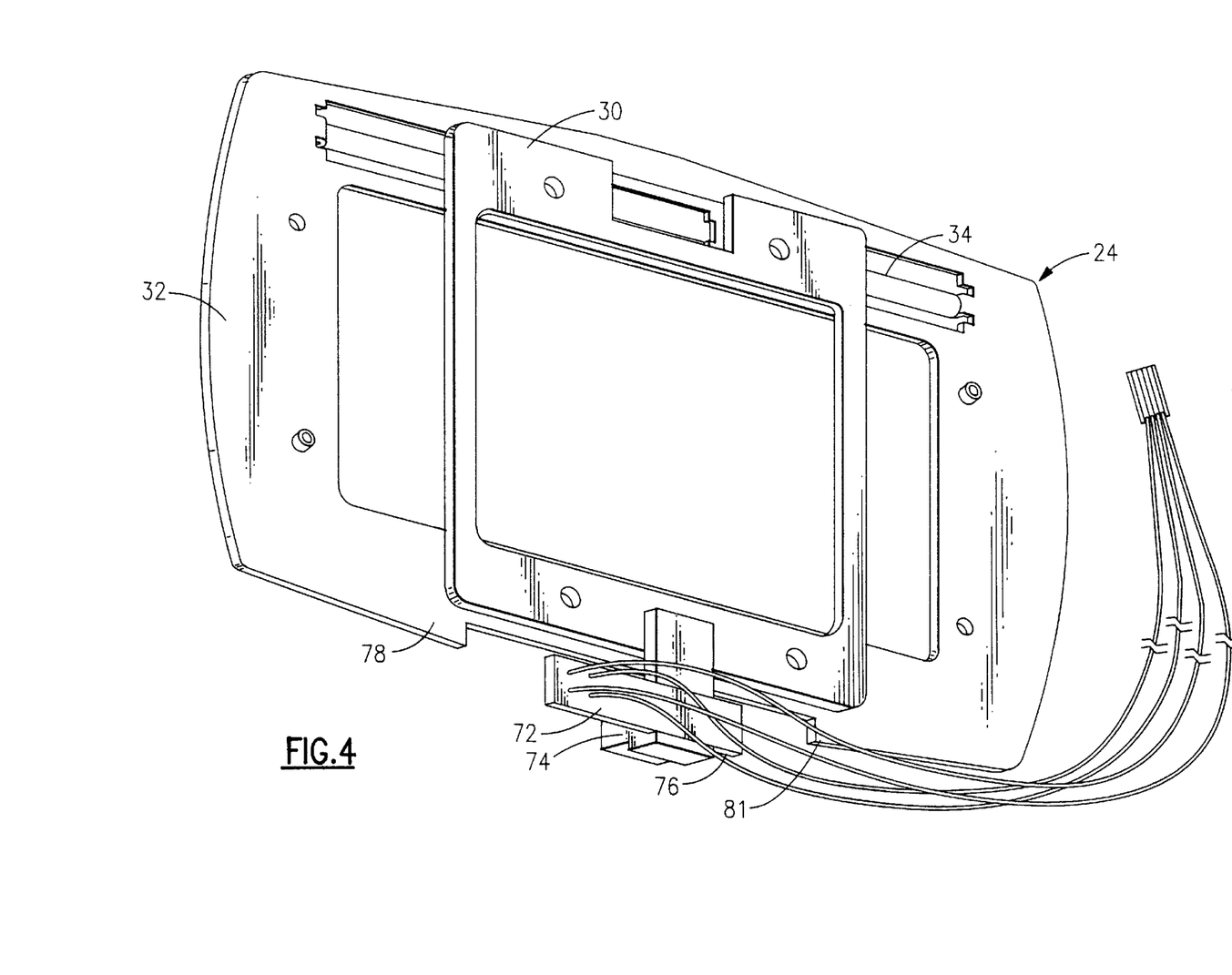
FIG. 4 is a rear perspective view of a view port according to the invention.
Figure 5:
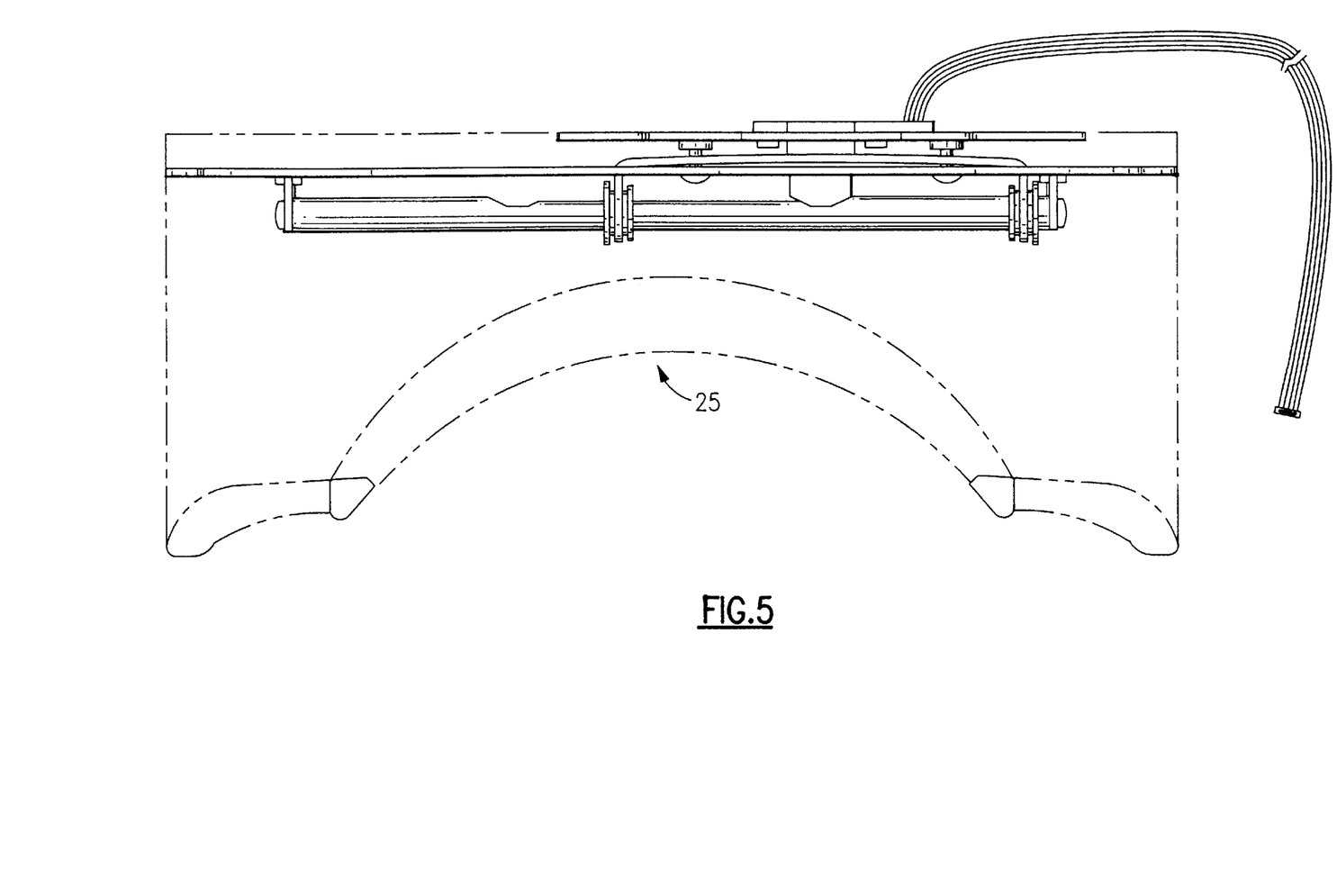
FIG. 5 is a top view of a view port according to the invention illustrating a view port casing in a first active position.
Figure 6:
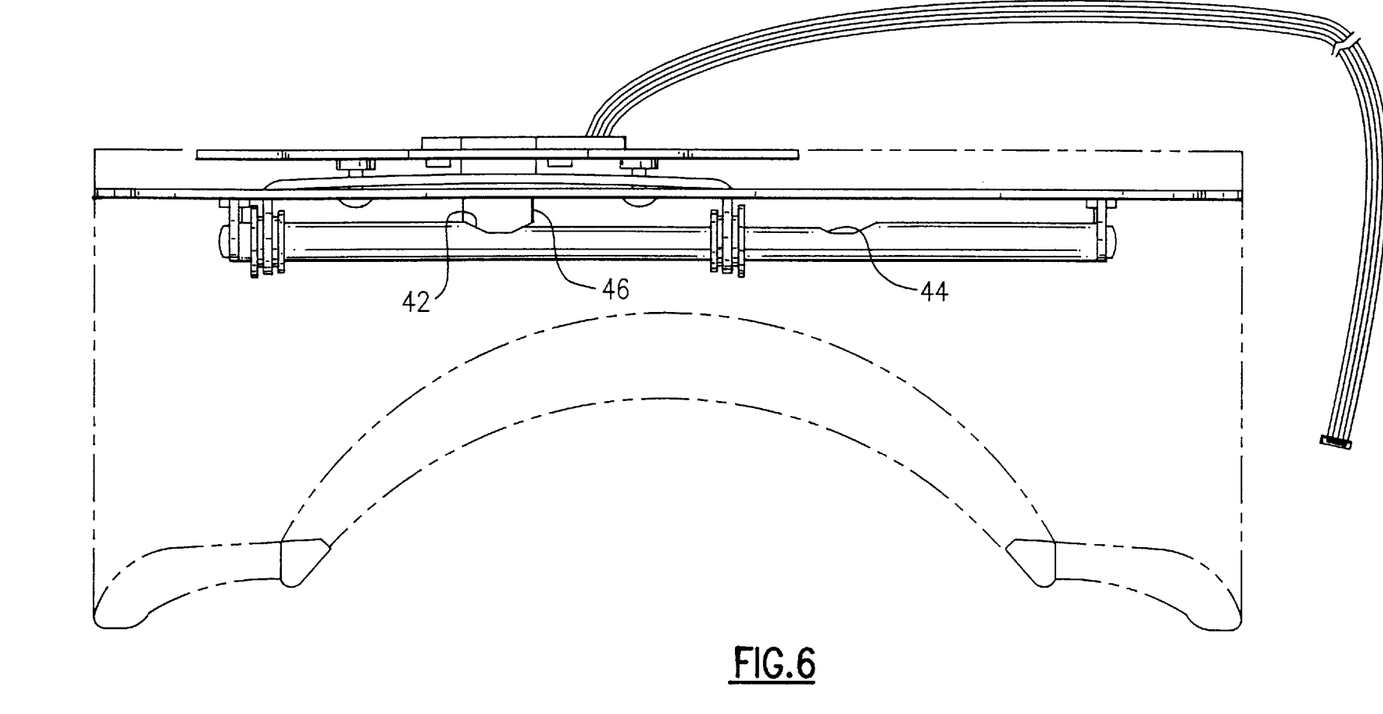
FIG. 6 is a top view of a view port according to the invention.

A possible arrangement for a sensor system according to the invention is best seen in FIGS. 3 and 4. In the embodiment shown, sensor system 58 includes a mounting member 72 rigidly mounted to a base frame 30. Mounting member 72 has mounted thereon a pair of electro-optical type position detectors 74 and 76, (which may be optical interrupt position detectors or photo detectors) for detecting the position of view port casing 26. When chassis 32 is in a first active position in relation to base frame 30, first position detector 74 is positioned directly opposite activating surface 78 so that position detector 74 emits an "on" state signal indicative of the chassis being in a first active position. When chassis 32 is in a second active position in relation to base frame 30 position detector 76 is positioned directly opposite second activating surface 81 so that detector 76 emits an "on" state signal indicative of the chassis being in a second active position. In the specific embodiment shown, each position detector 74 and 76 produces a single sensor output for input into control unit 12. The output condition wherein one sensor output is in an "on" state and the other sensor output is in an "off" state indicates that the view port is in active position in accordance with which sensor is in an "on" state. The output condition wherein neither sensor is in an "on" state indicates that the view port is in an inactive, intermediate position.

The sensor assembly could also comprise, for example, electromechanical switches arranged for sensing the positioning of the view port 20, magnetic switches, capacitive switches, or other types of electro-optical switches.

While the present invention has been explained with reference to a number of specific embodiments for the purpose of disclosing the best mode of making and carrying out the invention, it will be understood that the spirit and scope of the present invention should be determined with reference to the appended claims.

What is claimed is:

1. A view port for an eye test apparatus of the type having a single examination area, said view port comprising:
   a view port casing having a formation for receiving a patient's head;
   mounting means for mounting said view port to said apparatus;
   said mounting means allowing movement of said view port between a first active position wherein said formation receives a patient's head so that a patient's right eye is aligned with said examination area, and a second active position wherein said formation receives a patient's head so that a patient's left eye is aligned with said examination area.

2. The view port of claim 1, further comprising a sensor system for sensing a position of said casing.

3. The view port of claim 1, wherein said view port further includes a sensor system for sensing whether said casing is in one of either of said active positions.

4. The view port of claim 1, wherein said view port further includes a sensing assembly, said sensing assembly adapted to sense whether said casing is in said first position, and further adapted to sense whether said casing is in said second position.

5. An eye test apparatus of the type having a single examination area, said eye test apparatus comprising:
   a housing;
   a view port casing having a formation for receiving a patient's head;
   mounting means for mounting said view port to said housing, said mounting means permitting movement of said view port casing;
   a sensor system for sensing a present position of said view port casing; and
   a control unit responsive to said sensor system for controlling an administration of a test to a patient.

6. The eye test apparatus of claim 5, wherein said control unit is responsive to said sensor system so that administration of a test to a patient is permitted only if said sensor system indicates that said casing is in an active position.

7. The eye test apparatus of claim 5, wherein said mounting means permits movement of said view port casing between at least one active position and one inactive position, and wherein said control unit is responsive to said sensor system so that an administration of a test to a patient is permitted when said sensor system senses said casing is in said at least one active position.

8. The eye test apparatus of claim 5, wherein said control unit is responsive to said sensor system so that said control system abandons or pauses an administration of a test when said sensor system senses that said casing is in an inactive position.

9. The eye test apparatus of claim 5, wherein said mounting means permits movement of said view port casing between at least one active position and one inactive position, and wherein said control unit is responsive to said sensor system so that said control system abandons or pauses an administration of a test when said sensor system senses that said casing is in an inactive position.

10. The eye test apparatus of claim 5, wherein said control unit is responsive to said sensor system so that said control system administers a right-eye specific or a left-eye specific visual display to a user depending on a present output of said sensor system.

11. The eye test apparatus of claim 5, wherein said mounting means permits movement of said view port casing between a first, active position wherein said formation receives a patient's head so that a patient's right eye is aligned with said examination area, and a second active position wherein said formation receives a patient's head so that a patient's left eye is aligned with said examination area, and wherein said control unit is responsive to said sensor system so that said control unit administers a right-eye specific or a left-eye specific visual display to a user depending on a present output of said sensor system.

12. The eye test apparatus of claim 5, wherein said control unit is responsive to said sensor system so that said control unit automatically categorizes data captured thereby as right eye data or left eye data depending on a current output of said sensor system.

13. The eye test apparatus of claim 5, wherein said mounting means permits movement of said view port casing between a first, active position wherein said formation receives a patient's head so that a patient's right eye is aligned with said examination area, and a second active position wherein said formation receives a patient's head so that a patient's left eye is aligned with said examination area, and wherein said control unit is responsive to said sensor system so that said control unit categorizes data captured thereby as right eye data when said casing is in said first position, and categorizes data captured thereby as left eye data when said casing is in said second position.

14. The eye test apparatus of claim 5, wherein said mounting means permits movement of said view port casing between a first, active position wherein said formation receives a patient's head so that a patient's right eye is aligned with said examination area, and a second active position wherein said formation receives a patient's head so that a patient's left eye is aligned with said examination area.

15. The eye test apparatus of claim 5, wherein said mounting means permits movement of said view port casing between a first, active position wherein said formation receives a patient's head so that a patient's right eye is aligned with said examination area, and a second active position wherein said formation receives a patient's head so that a patient's left eye is aligned with said examination area, and wherein said sensor system senses whether said casing is in one of either of said active positions.

16. The eye test apparatus of claim 5, wherein said mounting means permits movement of said view port casing between a first, active position wherein said formation receives a patient's head so that a patient's right eye is aligned with said examination area, and a second active position wherein said formation receives a patient's head so that a patient's left eye is aligned with said examination area, wherein said sensing assembly is adapted to sense whether said casing is in said first position, and further wherein said sensing assembly is adapted to sense whether said casing is in said second position.

17. The apparatus of claim 5, wherein said view port casing further comprises:

a base end adapted for attachment to said eye test apparatus;

a top wall extending outwardly from said base end, said top wall having a top formation for receiving a patient's forehead, so that when said patient's forehead is received in said top formation, said patient's eyes are positioned approximately to a predetermined distance from said base end; and a pair of peripheral walls contiguous with said top wall and extending outwardly from said base end at least approximately to said predetermined distance, whereby ambient light is inhibited from entering an interior of said casing.

18. The view port casing of claim 17, wherein said top wall extends outwardly at least approximately to said predetermined distance.

19. The view port casing of claim 17, wherein said view port casing further includes a bottom wall extending outwardly from said base end, said bottom wall having a bottom formation for accommodating a patient's nose.

20. The view port casing of claim 17, wherein said view port casing further includes a bottom wall extending outwardly from said base end, said bottom wall having a bottom formation for accommodating a patient's nose, said bottom wall extending outwardly at least to said predetermined distance.

21. The view port casing of claim 17, wherein said view port is dimensioned so that when a patient whose forehead is received in said top formation is wearing commercially sized eyeglasses, said eyeglasses do not extend beyond a plane defined by said base end, and do not substantially contact said peripheral walls.

22. The view port casing of claim 17, wherein said view port includes a width dimension of at least about 6.9 inches and a height dimension of at least about 3.2 inches so that said casing is sized to accommodate a patient wearing commercially-sized eyeglasses.

23. The view port casing of claim 17 wherein substantially an entire interior surface of said casing is colored a light absorbing color.

24. The view port casing of claim 17 wherein said formation is of a substantially curved shape formed about a center of said top wall so that a head received in said casing is guided approximately toward a center of said top wall.

25. A view port casing for an eye test apparatus, said view port casing comprising:

a base end adapted for attachment to said eye test apparatus;

a top wall extending outwardly from said base end, said top wall having a top formation for receiving a patient's forehead, so that when said patient's forehead is received in said top formation, said patient's eyes are positioned approximately to a predetermined distance from said base end; and a pair of peripheral walls contiguous with said top wall and extending outwardly from said base end at least approximately to said predetermined distance, whereby ambient light is inhibited from entering an interior of said casing.

26. The view port casing of claim 25, wherein said top wall extends outwardly at least approximately to said predetermined distance.

27. The view port casing of claim 25, wherein said view port casing further includes a bottom wall extending outwardly from said base end, said bottom wall having a bottom formation for accommodating a patient's nose.

28. The view port casing of claim 25, wherein said view port casing further includes a bottom wall extending outwardly from said base end, said bottom wall having a bottom formation for accommodating a patient's nose, said bottom wall extending outwardly at least to said predetermined distance.

29. The view port casing of claim 25, wherein said view port casing is dimensioned so that when a patient whose forehead is received in said top formation is wearing commercially sized eyeglasses, said eyeglasses do not extend beyond a plane defined by said base end, and do not substantially contact said peripheral walls.

30. The view port casing of claim 25, wherein said view port casing includes a width dimension of at least about 6.9 inches and a height dimension of at least about 3.2 inches so that said casing is sized to accommodate a patient wearing commercially-sized eyeglasses.

31. The view port casing of claim 25 wherein substantially an entire interior surface of said casing is colored a light absorbing color.

32. The view port casing of claim 25 wherein said formation is of a substantially curved shape formed about a center of said top wall so that a head received in said casing is guided approximately toward a center of said top wall.

33. An eye test apparatus of the type having a single examination area, said apparatus comprising:

a housing;

a view port casing having a formation for receiving a patient's head;

mounting means for mounting said view port to said housing;

said mounting means allowing movement of said view port between a first active position wherein said formation receives a patient's head so that a patient's right eye is aligned with said examination area, and a second active position wherein said formation receives a patient's head so that a patient's left eye is aligned with said examination area.

34. The eye test apparatus of claim 33, wherein said apparatus further includes a shield disposed about said examination area, for occluding said examination area from an eye not being tested.

35. The eye test apparatus of claim 33, wherein said formation is adapted to receive a patient's forehead at a center of said casing.

36. The apparatus of claim 33, wherein said view port casing further comprises:

a base end adapted for attachment to said eye test apparatus;

a top wall extending outwardly from said base end, said top wall having a top formation for receiving a patient's forehead, so that when said patient's forehead is received in said top formation, said patient's eyes are positioned approximately to a predetermined distance from said base end; and a pair of peripheral walls contiguous with said top wall and extending outwardly from said base end at least approximately to said predetermined distance, whereby ambient light is inhibited from entering an interior of said casing.

37. The view port casing of claim 36, wherein said top wall extends outwardly at least approximately to said predetermined distance.

38. The view port casing of claim 36, wherein said view port casing further includes a bottom wall extending outwardly from said base end, said bottom wall having a bottom formation for accommodating a patient's nose.

39. The view port casing of claim 36, wherein said view port casing further includes a bottom wall extending outwardly from said base end, said bottom wall having a bottom formation for accommodating a patient's nose, said bottom wall extending outwardly at least to said predetermined distance.

40. The view port casing of claim 36, wherein said view port is dimensioned so that when a patient whose forehead is received in said top formation is wearing commercially sized eyeglasses, said eyeglasses do not extend beyond a plane defined by said base end, and do not substantially contact said peripheral walls.

41. The view port casing of claim 36, wherein said view port includes a width dimension of at least about 6.9 inches and a depth dimension of at least about 3.2 inches so that said casing is sized to accommodate a patient wearing commercially-sized eyeglasses.

42. The view port casing of claim 36 wherein substantially an entire interior surface of said casing is colored a light absorbing color.

43. The view port casing of claim 36 wherein said formation is of a substantially curved shape formed about a center of said top wall so that a head received in said casing is guided approximately toward a center of said top wall.

* * * * *